US007550471B2

(12) United States Patent
Blasco et al.

(10) Patent No.: US 7,550,471 B2
(45) Date of Patent: Jun. 23, 2009

(54) 5-ALKYL-7-AMINOTRIAZOLOPYRIMIDINES, METHODS AND INTERMEDIARY PRODUCT NECESSARY FOR THE PRODUCTION THEREOF, AGENTS CONTAINING SAID COMPOUNDS AND THE USE THEREOF FOR FIGHTING AGAINST HARMFUL MUSHROOMS

(75) Inventors: Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Heβheim (DE); Anja Schwögler, Mannheim (DE); Eberhard Ammermann, Heppenheim (DE); Siegfried Strathmann, Limburgerhof (DE); Ulrich Schöfl, Brühl (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 284 days.

(21) Appl. No.: 10/531,981

(22) PCT Filed: Nov. 4, 2003

(86) PCT No.: PCT/EP03/12277

§ 371 (c)(1), (2), (4) Date: Apr. 20, 2005

(87) PCT Pub. No.: WO2004/041825

PCT Pub. Date: May 21, 2004

(65) Prior Publication Data

US 2005/0272749 A1 Dec. 8, 2005

(30) Foreign Application Priority Data

Nov. 7, 2002 (DE) ................................ 102 52 261

(51) Int. Cl.
*A01N 43/90* (2006.01)
*A61K 31/519* (2006.01)
*C07D 487/00* (2006.01)

(52) U.S. Cl. ................................ 514/259.31; 544/263

(58) Field of Classification Search ............ 514/259.31; 544/263
See application file for complete search history.

(56) References Cited

U.S. PATENT DOCUMENTS 2,444,605 A * 7/1948 Heimbach et al. ........... 430/615
5,965,561 A * 10/1999 Pees et al. ................ 514/259.4
2005/0261314 A1* 11/2005 i Blasco et al. ........ 514/259.31

FOREIGN PATENT DOCUMENTS

EP 0 141 317 A2 5/1985
WO WO-02/083677 A1 10/2002

* cited by examiner

*Primary Examiner*—James O Wilson
*Assistant Examiner*—Jeffrey H Murray
(74) *Attorney, Agent, or Firm*—Birch, Stewart, Kolasch & Birch, LLP

(57) ABSTRACT

The invention relates to 5-alkyl-7-aminotriazolopyrimidines of the formula (I) and to the salts thereof. In said formula substituents have the following meanings: $R^1$ and $R^2$ each is a hydrogen atom or a group of alkyl, alcenyl, haloalkyl, cycloalky, phenyl or naphtyle, saturated, unstaturated or aromatic heterocycle having from five to six members which contain from one to four nitrogen atoms or one to three nitrogen atoms and one sulfur or oxygen atom, or $R^1$ and $R^2$ can from together with a connecting them nitrogen atom a cycle of 5 to 6 members containing from one to four nitrogen atoms or from one to three nitrogen atoms and one sulfur or oxygen atom, $R^3$ is a cycloalkyl or bicycloalkyl group, $R^1$, $R^2$ and $R^3$ can be substituted in conformity with a description, and X is an alkyl or alkyl halide group. The inventive methods and intermediary products necessary for producing said compounds, agents containing them and the use therefore for fighting against harmful mushroom are also disclosed.

(I)

$R^1$, $R^2$, N, $R^3$, N, N, N, N, X

9 Claims, No Drawings

5-ALKYL-7-AMINOTRIAZOLOPYRIMIDINES, METHODS AND INTERMEDIARY PRODUCT NECESSARY FOR THE PRODUCTION THEREOF, AGENTS CONTAINING SAID COMPOUNDS AND THE USE THEREOF FOR FIGHTING AGAINST HARMFUL MUSHROOMS

FIELD OF INVENTION

The present invention relates to 5-alkyl-7-aminotriazolopyrimidines of the formula I,

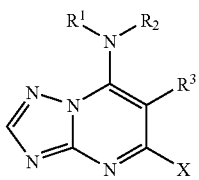

where:

$R^1$, $R^2$ are hydrogen, $C_1$-$C_{10}$-alkyl, $C_2$-$C_{10}$-alkenyl, $C_2$-$C_{10}$-alkynyl, $C_1$-$C_{10}$-haloalkyl, $C_3$-$C_8$-cycloalkyl, phenyl, naphthyl; or 5- or 6-membered saturated, unsaturated or aromatic heterocyclyl which contains one to four nitrogen atoms or one to three nitrogen atoms and one sulfur or oxygen atom; or $R^1$ and $R^2$ together with the bridging nitrogen atom can form a 5- or 6-membered ring which contains one to four nitrogen atoms or one to three nitrogen atoms and one sulfur or oxygen atom;

if $R^1$ and $R^2$ are not hydrogen they can, independently of one another, be partially or fully halogenated and/or may carry one to three radicals from the group $R^a$ $R^a$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and unhalogenated or halogenated oxy-$C_1$-$C_4$-alkyleneoxy;

where these aliphatic, alicyclic or aromatic groups for their part may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkyl-sulfonyl, alkylsulfoxyl, alkoxycarbonyl, alkylcarbonyloxy, alkylaminocarbonyl, dialkyl-aminocarbonyl, alkylaminothiocarbonyl, dialkyl-aminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl, heterocyclyloxy, where the cyclic systems contain 3 to 10 ring members; aryl, aryloxy, arylthio, aryl-$C_1$-$C_6$-alkoxy, aryl-$C_1$-$C_6$-alkyl, hetaryl, hetaryloxy, hetarylthio, where the aryl radicals preferably contain 6 to 10 ring members, the hetaryl radicals contain 5 or 6 ring members, where the cyclic systems may be partially or fully halogenated or may be substituted by alkyl or haloalkyl groups;

$R^3$ is $C_3$-$C_{14}$-cycloalkyl or $C_6$-$C_{14}$-bicycloalkyl, where $R^3$ may be unsubstituted or partially or fully halogenated and/or may carry one to three radicals from the group $R^a$; and X is $C_1$-$C_6$-alkyl or $C_1$-$C_2$-haloalkyl;

and their salts.

Additionally, the invention relates to processes and intermediates for preparing the compounds I, and to compositions and to the use of the compounds I for controlling phytopathogenic harmful fungi.

DESCRIPTION OF RELATED ART

6-Aryltriazolopyrimidines are disclosed in WO 98/46608 and EP-A 550 113. 6-Benzyltriazolopyrimidines which are substituted in a specific manner by aromatic groups and have pharmaceutical action are known from U.S. Pat. No. 5,231,094 and U.S. Pat. No. 5,387,747. EP-A 141 317 discloses 6-aryl- and 6-arylalkyl-7-aminotriazolopyrimidines which may carry an alkyl radical in the 5-position. 6-Cycloalkyltriazolopyrimidines having various radicals in the 5-position are mentioned in EP-A 613 900. 5-Alkyl-6-phenyl-7-aminotriazolopyrimidines are known from U.S. Pat. No. 5,994,360.

The compounds described in WO 98/46608, EP-A 550 113, EP-A 141 317, EP-A 613 900 and U.S. Pat. No. 5,994,360 are suitable for use as crop treatment agents against harmful fungi.

However, in many cases their action is unsatisfactory. It is an object of the present invention to provide compounds having improved activity.

SUMMARY OF THE INVENTION

This object has been achieved by the 5-alkyl-7-aminotriazolopyrimidines of the formula I. Furthermore, we have found intermediates and processes for preparing the compounds I, and the use of the compounds I and of compositions comprising them for controlling phytopathogenic harmful fungi.

The compounds of the formula I differ from the compounds known from the publications mentioned above by the combination of the 5-alkyl group with the mono- or bicyclic cycloalkyl group $R^3$ on the triazolopyrimidine skeleton.

DETAILED DESCRIPTION OF THE INVENTION

7-Aminotriazolopyrimidines of the formula I can be obtained advantageously by reacting 3-amino-1,2,4-triazole with dicarbonyl compounds of the formula II where A is $C_1$-$C_{10}$-alkoxy, in particular $C_1$-$C_4$-alkoxyl, and $R^3$ and X are as defined for formula I, to give 7-hydroxytriazolopyrimidines of the formula III:

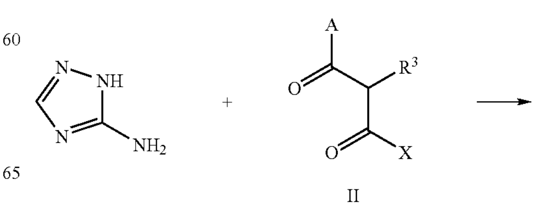

-continued

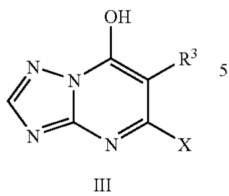

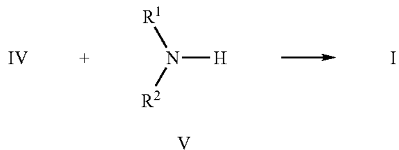

This reaction is usually carried out at temperatures of from 25° C. to 210° C., preferably from 120° C. to 180° C., in the presence of a base [cf. EP-A-770 615].

Suitable bases are, in general, organic bases, for example tertiary amines such as trimethylamine, triethylamine, triisopropylamine, tributylamine and N-methylpiperidine and pyridine. Particular preference is given to triethylamine and tributylamine.

In general, the bases are employed in catalytic amounts; however, they can also be employed in equimolar amounts, in excess or, if appropriate, as solvent.

The starting materials are generally reacted with one another in equimolar amounts. In terms of yield, it may be advantageous to employ an excess of II, based on the aminotriazole.

The starting materials required for preparing the compounds I are known from the literature or can be prepared in accordance with the literature cited [Heterocycl. 1996, 1031; Tetrahedron Lett. 24 (1966), 2661; Chem. Pharm. Bull. 1961, 801], or they are commercially available.

The 7-hydroxytriazolopyrimidines of the formula III are then reacted with a halogenating agent to give 7-halotriazolopyrimidines of the formula IV:

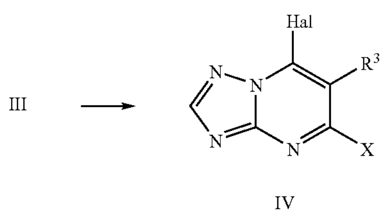

This reaction is usually carried out at temperatures of from 0° C. to 150° C., preferably from 80° C. to 125° C., in an inert organic solvent or in the absence of a solvent [cf. EP-A-770 615].

Preferred halogenating agents are brominating or chlorinating agents, such as, for example, phosphorus oxybromide or phosphorus oxychloride, neat or in the presence of a solvent.

Suitable solvents are aliphatic hydrocarbons, such as pentane, hexane, cyclohexane and petroleum ether, aromatic hydrocarbons, such as toluene, o-, m- and p-xylene, particularly preferably toluene, o-, m- and p-xylene. It is also possible to use mixtures of the solvents mentioned.

The halotriazolopyrimidines of the formula IV are reacted with an amine of the formula V to give 7-aminotriazolopyrimidines of the formula I.

This reaction is usually carried out at temperatures of from 0° C. to 70° C., preferably from 10° C. to 35° C., in an inert organic solvent in the presence of a base [cf. EP-A 550 113].

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran.

Suitable bases are, in general, inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides and also alkali metal and alkaline earth metal alkoxides and dimethoxymagnesium, moreover organic bases, for example tertiary amines, such as trimethylamine, triethylamine, triisopropylamine and N-methylpiperidine, pyridine, substituted pyridines and also bicyclic amines. Particular preference is given to triethylamine, potassium carbonate and sodium carbonate.

The bases are generally employed in catalytic amounts; however, they can also be used in equimolar amounts, in excess or, if appropriate, as solvent. Alternatively, an excess of the compound V may serve as base.

The starting materials are generally reacted with one another in equimolar amounts. In terms of yield, it may be advantageous to employ an excess of V, based on IV.

The reaction mixtures are worked up in a customary manner, for example by mixing with water, separating the phases and, if appropriate, chromatographic purification of the crude products. In some cases, the intermediates and end products are obtained in the form of colorless or slightly brownish viscous oils which can be freed from volatile components or purified under reduced pressure and at moderately elevated temperatures. If the intermediates and end products are obtained as solids, purification can also be carried out by recrystallization or digestion.

If individual compounds I are not obtainable by the routes described above, they can be prepared by derivatization of other compounds I.

7-Hydroxy- and 7-halotriazolopyrimidines of the formulae III and IV, respectively, where X and $R^3$ are as defined in formula I and Hal is halogen, in particular chlorine or bromine, are novel.

In the definitions of the symbols given in the formulae above, collective terms were used which, in a general manner, represent the following substituents:

halogen: fluorine, chlorine, bromine and iodine;

alkyl: saturated, straight-chain or branched hydrocarbon radicals having 1 to 4, 6, 8 or 10 carbon atoms, for example $C_1$-$C_6$-alkyl, such as methyl, ethyl, propyl, 1-methylethyl, butyl, 1-methyl-propyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethyl-butyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 10 carbon atoms (as mentioned above), where some, for example one to three, or all of the hydrogen atoms in these groups may be replaced by halogen atoms as mentioned above, for example $C_1$-$C_2$-haloalkyl, such as chloromethyl, bromomethyl, dichloro-methyl, trichloromethyl, fluoromethyl, difluoromethyl, trifluoro-methyl, chlorofluoromethyl, dichlorofluoromethyl, chlorodifluoro-methyl, 1-chloroethyl, 1-bromoethyl, 1-fluoroethyl, 2-fluoro-ethyl, 2,2-difluoroethyl, 2,2,2-trifluoroethyl, 2-chloro-2-fluoroethyl, 2-chloro-2,2-difluoroethyl, 2,2-dichloro-2-fluoro-ethyl, 2,2,2-trichloroethyl and pentafluoroethyl;

alkenyl: unsaturated, straight-chain or branched hydrocarbon radicals having 2 to 6 or 10 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 6 or 10 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic, saturated hydrocarbon groups having 3 to 5, 6 or 8 carbon ring members, for example $C_3$-$C_8$-cycloalkyl, such as cyclopropyl, cyclobutyl, cyclopentyl, cyclohexyl, cycloheptyl and cyclooctyl;

bicycloalkyl: bicyclic, saturated hydrocarbon groups having 6 to 14, in particular 7 or 10, carbon ring members, which groups consist of fused 5-, 6- and/or 7-membered ring systems.

5- or 6-membered heterocyclyl (saturated heterocyclyl) which comprises one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydro-pyrimidinyl, 5-hexahydropyrimidinyl and 2-piperazinyl;

5- or 6-membered heterocyclyl (unsaturated heterocyclyl) which comprises one to three nitrogen atoms and/or one oxygen or sulfur atom or one or two oxygen and/or sulfur atoms and one or two C═C double bonds, for example 3,6-dihydro-2H-pyridin-1-yl or 2,5-dihydropyrrol-1-yl;

5-membered heteroaryl (aromatic heterocyclyl) which comprises one to four nitrogen atoms or one to three nitrogen atoms and one sulfur or oxygen atom: 5-membered heteroaryl groups which, in addition to carbon atoms, may comprise one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;

6-membered heteroaryl (aromatic heterocyclyl) which comprises one to three or one to four nitrogen atoms: 6-membered heteroaryl groups which, in addition to carbon atoms, may comprise one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl;

oxyalkyleneoxy: divalent unbranched chains of 1 to 3 $CH_2$ groups, where both valences are attached to the skeleton via an oxygen atom, for example $OCH_2O$, $OCH_2CH_2O$ and $OCH_2CH_2CH_2O$.

The compounds of the formula I can also be present in the form of their agriculturally useful salts, where the type of salt is generally not important. Suitable salts are, in general, the salts of those cations or the acid addition salts of those acids whose cations and anions, respectively, have no adverse effect on the fungicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl. Preference is given to ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogensulfate, sulfate, dihydrogenphosphate, hydrogenphosphate, nitrate, hydrogencarbonate, carbonate, hexafluorosilicate, hexafluorophosphate, benzoate, and the anions of $C_1$-$C_4$-alkanoic acids, preferably formate, acetate, propionate and butyrate.

If $R^1$ and/or $R^2$ have/has a center of chirality, the (R)- and (S)-isomers and the racemates of the compounds of the formula I are included in the scope of the invention.

With respect to the variables, the particularly preferred embodiments of the intermediates correspond to those of radicals $R^3$ and X in formula I.

With a view to the intended use of the 5-alkyl-7-aminotriazolo-pyrimidines of the formula I, particular preference is given to the following meanings of the substituents, in each case on their own or in combination:

Preference is given to compounds I in which $R^1$ and $R^2$ are hydrogen, $C_1$-$C_{10}$-alkyl or $C_1$-$C_6$-haloalkyl, in particular hydrogen, $C_1$-$C_6$-alkyl or $C_1$-$C_4$-haloalkyl and with particular preference hydrogen, 1-methylpropyl, isopropyl or 1,1,1-trifluoro-2-propyl.

Preference is also given to compounds I in which $R^1$ and $R^2$ together with the bridging nitrogen atom form a 5-or 6-membered ring which may contain an oxygen or sulfur atom, such as pyrrolidin-1-yl, pyrrol-1-yl, pyrazol-1-yl, imidazol-1-yl, piperidin-1-yl, morpholin-4-yl, thiomorpholin-4-yl, 3,6-dihydro-2H-pyridin-1-yl, 2,5-dihydropyrrol-1-yl, where the radicals mentioned may be substituted by one to three groups $R^a$, in particular by $C_1$-$C_4$-alkyl, such as, for example, methyl or ethyl. Particular preference is given to compounds I in which $R^1$ and $R^2$ together form a 4-methylpiperidin-1-yl group.

Special preference is given to compounds I in which $R^1$ is not hydrogen.

In addition, particular preference is also given to compounds I in which $R^1$ is hydrogen, $C_1$-$C_6$-alkyl or $C_1$-$C_4$-haloalkyl and $R^2$ is hydrogen or $C_1$-$C_4$-alkyl, in particular hydrogen.

Preference is furthermore given to compounds I in which $R^1$ and $R^2$ do not carry any groups $R^b$, in particular to those in which $R^1$ and $R^2$ do not carry any groups $R^a$.

A further preferred object are compounds I in which $R^1$ and $R^2$ are hydrogen.

Particular preference is also given to compounds I in which $R^3$ is $C_3$-$C_{12}$-cycloalkyl, preferably cyclopropyl, cyclopentyl, cyclohexyl, cyclooctyl or cyclododecyl, or bicycloheptyl, where $R^3$ may carry one to three groups $R^a$. In particular, $R^3$ is unsubstituted.

Moreover, particular preference is given to compounds I in which X is $C_1$-$C_4$-alkyl, in particular methyl.

With a view to their use, particular preference is given to the compounds I compiled in the tables below. Moreover, the groups mentioned for a substituent in the tables are per se, independently of the combination in which they are mentioned, a particularly preferred embodiment of the substituent in question.

Table 1

Compounds of the formula I in which $R^3$ is cyclopropyl, X is methyl and the combination of the radicals $R^1$ and $R^2$ for a compound corresponds in each case to one row of Table A Table 2

Compounds of the formula I in which $R^3$ is cyclopropyl, X is ethyl and the combination of the radicals $R^1$ and $R^2$ for a compound corresponds in each case to one row of Table A Table 3

Compounds of the formula I in which $R^3$ is cyclopropyl, X is n-propyl and the combination of the radicals $R^1$ and $R^2$ for a compound corresponds in each case to one row of Table A Table 4

Compounds of the formula I in which $R^3$ is cyclopropyl, X is isopropyl and the combination of the radicals $R^1$ and $R^2$ for a compound corresponds in each case to one row of Table A Table 5

Compounds of the formula I in which $R^3$ is cyclopentyl, X is methyl and the combination of the radicals $R^1$ and $R^2$ for a compound corresponds in each case to one row of Table A Table 6

Compounds of the formula I in which $R^3$ is cyclopentyl, X is ethyl and the combination of the radicals $R^1$ and $R^2$ for a compound corresponds in each case to one row of Table A Table 7

Compounds of the formula I in which $R^3$ is cyclopentyl, X is n-propyl and the combination of the radicals $R^1$ and $R^2$ for a compound corresponds in each case to one row of Table A Table 8

Compounds of the formula I in which $R^3$ is cyclopentyl, X is isopropyl and the combination of the radicals $R^1$ and $R^2$ for a compound corresponds in each case to one row of Table A Table 9

Compounds of the formula I in which $R^3$ is cyclohexyl, X is methyl and the combination of the radicals $R^1$ and $R^2$ for a compound corresponds in each case to one row of Table A Table 10

Compounds of the formula I in which $R^3$ is cyclohexyl, X is ethyl and the combination of the radicals $R^1$ and $R^2$ for a compound corresponds in each case to one row of Table A Table 11

Compounds of the formula I in which $R^3$ is cyclohexyl, X is n-propyl and the combination of the radicals $R^1$ and $R^2$ for a compound corresponds in each case to one row of Table A Table 12

Compounds of the formula I in which $R^3$ is cyclohexyl, X is isopropyl and the combination of the radicals $R^1$ and $R^2$ for a compound corresponds in each case to one row of Table A Table 13

Compounds of the formula I in which $R^3$ is cycloheptyl, X is methyl and the combination of the radicals $R^1$ and $R^2$ for a compound corresponds in each case to one row of Table A Table 14

Compounds of the formula I in which $R^3$ is cycloheptyl, X is ethyl and the combination of the radicals $R^1$ and $R^2$ for a compound corresponds in each case to one row of Table A Table 15

Compounds of the formula I in which $R^3$ is cycloheptyl, X is n-propyl and the combination of the radicals $R^1$ and $R^2$ for a compound corresponds in each case to one row of Table A Table 16

Compounds of the formula I in which $R^3$ is cycloheptyl, X is isopropyl and the combination of the radicals $R^1$ and $R^2$ for a compound corresponds in each case to one row of Table A Table 17

Compounds of the formula I in which $R^3$ is cyclooctyl, X is methyl and the combination of the radicals $R^1$ and $R^2$ for a compound corresponds in each case to one row of Table A Table 18

Compounds of the formula I in which $R^3$ is cyclooctyl, X is ethyl and the combination of the radicals $R^1$ and $R^2$ for a compound corresponds in each case to one row of Table A Table 19

Compounds of the formula I in which $R^3$ is cyclooctyl, X is n-propyl and the combination of the radicals $R^1$ and $R^2$ for a compound corresponds in each case to one row of Table A Table 20

Compounds of the formula I in which $R^3$ is cyclooctyl, X is isopropyl and the combination of the radicals $R^1$ and $R^2$ for a compound corresponds in each case to one row of Table A Table 21

Compounds of the formula I in which $R^3$ is cyclododectyl, X is methyl and the combination of the radicals $R^1$ and $R^2$ for a compound corresponds in each case to one row of Table A Table 22

Compounds of the formula I in which $R^3$ is cyclododectyl, X is ethyl and the combination of the radicals $R^1$ and $R^2$ for a compound corresponds in each case to one row of Table A Table 23

Compounds of the formula I in which $R^3$ is cyclododectyl, X is n-propyl and the combination of the radicals $R^1$ and $R^2$ for a compound corresponds in each case to one row of Table A Table 24

Compounds of the formula I in which $R^3$ is cyclododectyl, X is isopropyl and the combination of the radicals $R^1$ and $R^2$ for a compound corresponds in each case to one row of Table A Table 25

Compounds of the formula I in which $R^3$ is bicyclo[2.2.1]hept-2-yl, X is methyl and the combination of the radicals $R^1$ and $R^2$ for a compound corresponds in each case to one row of Table A Table 26

Compounds of the formula I in which $R^3$ is bicyclo[2.2.1]hept-2-yl, X is ethyl and the combination of the radicals $R^1$ and $R^2$ for a compound corresponds in each case to one row of Table A Table 27

Compounds of the formula I in which $R^3$ is bicyclo[2.2.1]hept-2-yl, X is n-propyl and the combination of the radicals $R^1$ and $R^2$ for a compound corresponds in each case to one row of Table A Table 28

Compounds of the formula I in which $R^3$ is bicyclo[2.2.1]hept-2-yl, X is isopropyl and the combination of the radicals $R^1$ and $R^2$ for a compound corresponds in each case to one row of Table A Table 29

Compounds of the formula I in which $R^3$ is 2-methylcyclopentyl, X is methyl and the combination of the radicals $R^1$ and $R^2$ for a compound corresponds in each case to one row of Table A Table 30

Compounds of the formula I in which $R^3$ is 2-methylcyclopentyl, X is ethyl and the combination of the radicals $R^1$ and R2 for a compound corresponds in each case to one row of Table A Table 31

Compounds of the formula I in which $R^3$ is 2-methylcyclopentyl, X is n-propyl and the combination of the radicals $R^1$ and $R^2$ for a compound corresponds in each case to one row of Table A Table 32

Compounds of the formula I in which $R^3$ is 2-methylcyclopentyl, X is isopropyl and the combination of the radicals $R^1$ and $R^2$ for a compound corresponds in each case to one row of Table A Table 33

Compounds of the formula I in which $R^3$ is 3-methylcyclopentyl, X is methyl and the combination of the radicals $R^1$ and $R^2$ for a compound corresponds in each case to one row of Table A Table 34

Compounds of the formula I in which $R^3$ is 3-methylcyclopentyl, X is ethyl and the combination of the radicals $R^1$ and $R^2$ for a compound corresponds in each case to one row of Table A Table 35

Compounds of the formula I in which $R^3$ is 3-methylcyclopentyl, X is n-propyl and the combination of the radicals $R^1$ and $R^2$ for a compound corresponds in each case to one row of Table A Table 36

Compounds of the formula I in which $R^3$ is 3-methylcyclopentyl, X is isopropyl and the combination of the radicals $R^1$ and $R^2$ for a compound corresponds in each case to one row of Table A Table 37

Compounds of the formula I in which $R^3$ is 2-methylcyclohexyl, X is methyl and the combination of the radicals $R^1$ and $R^2$ for a compound corresponds in each case to one row of Table A Table 38

Compounds of the formula I in which $R^3$ is 2-methylcyclohexyl, X is ethyl and the combination of the radicals $R^1$ and $R^2$ for a compound corresponds in each case to one row of Table A Table 39

Compounds of the formula I in which $R^3$ is 2-methylcyclohexyl, X is n-propyl and the combination of the radicals $R^1$ and $R^2$ for a compound corresponds in each case to one row of Table A Table 40

Compounds of the formula I in which $R^3$ is 2-methylcyclohexyl, X is isopropyl and the combination of the radicals $R^1$ and $R^2$ for a compound corresponds in each case to one row of Table A Table 41

Compounds of the formula I in which $R^3$ is 3-methylcyclohexyl, X is methyl and the combination of the radicals $R^1$ and $R^2$ for a compound corresponds in each case to one row of Table A Table 42

Compounds of the formula I in which $R^3$ is 3-methylcyclohexyl, X is ethyl and the combination of the radicals $R^1$ and $R^2$ for a compound corresponds in each case to one row of Table A Table 43

Compounds of the formula I in which $R^3$ is 3-methylcyclohexyl, X is n-propyl and the combination of the radicals $R^1$ and $R^2$ for a compound corresponds in each case to one row of Table A Table 44

Compounds of the formula I in which $R^3$ is 3-methylcyclohexyl, X is isopropyl and the combination of the radicals $R^1$ and $R^2$ for a compound corresponds in each case to one row of Table A Table 45

Compounds of the formula I in which $R^3$ is 4-methylcyclohexyl, X is methyl and the combination of the radicals $R^1$ and $R^2$ for a compound corresponds in each case to one row of Table A Table 46

Compounds of the formula I in which $R^3$ is 4-methylcyclohexyl, X is ethyl and the combination of the radicals $R^1$ and $R^2$ for a compound corresponds in each case to one row of Table A Table 47

Compounds of the formula I in which $R^3$ is 4-methylcyclohexyl, X is n-propyl and the combination of the radicals $R^1$ and $R^2$ for a compound corresponds in each case to one row of Table A Table 48

Compounds of the formula I in which $R^3$ is 4-methylcyclohexyl, X is isopropyl and the combination of the radicals $R^1$ and $R^2$ for a compound corresponds in each case to one row of Table A

TABLE A

I

| No. | $R^1$ | $R^2$ |
|---|---|---|
| A-1 | H | H |
| A-2 | $CH_2CH_3$ | H |
| A-3 | $CH_2CH_3$ | $CH_3$ |
| A-4 | $CH_2CH_3$ | $CH_2CH_3$ |
| A-5 | $CH_2CF_3$ | H |
| A-6 | $CH_2CF_3$ | $CH_3$ |
| A-7 | $CH_2CF_3$ | $CH_2CH_3$ |
| A-8 | $CH_2CCl_3$ | H |
| A-9 | $CH_2CCl_3$ | $CH_3$ |
| A-10 | $CH_2CCl_3$ | $CH_2CH_3$ |
| A-11 | $CH_2CH_2CH_3$ | H |
| A-12 | $CH_2CH_2CH_3$ | $CH_3$ |
| A-13 | $CH_2CH_2CH_3$ | $CH_2CH_3$ |
| A-14 | $CH_2CH_2CH_3$ | $CH_2CH_2CH_3$ |
| A-15 | $CH(CH_3)_2$ | H |
| A-16 | $CH(CH_3)_2$ | $CH_3$ |
| A-17 | $CH(CH_3)_2$ | $CH_2CH_3$ |
| A-18 | (R/S) $CH(CH_3)$—$CH_2CH_3$ | H |
| A-19 | (R/S) $CH(CH_3)$—$CH_2CH_3$ | $CH_3$ |
| A-20 | (R/S) $CH(CH_3)$—$CH_2CH_3$ | $CH_2CH_3$ |
| A-21 | (R) $CH(CH_3)$—$CH_2CH_3$ | H |
| A-22 | (R) $CH(CH_3)$—$CH_2CH_3$ | $CH_3$ |
| A-23 | (R) $CH(CH_3)$—$CH_2CH_3$ | $CH_2CH_3$ |
| A-24 | (S) $CH(CH_3)$—$CH_2CH_3$ | H |
| A-25 | (S) $CH(CH_3)$—$CH_2CH_3$ | $CH_3$ |
| A-26 | (S) $CH(CH_3)$—$CH_2CH_3$ | $CH_2CH_3$ |
| A-27 | (R/S) $CH(CH_3)$—$CH(CH_3)_2$ | H |

TABLE A-continued

I

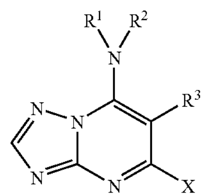

| No. | $R^1$ | $R^2$ |
|---|---|---|
| A-28 | (R/S) $CH(CH_3)$—$CH(CH_3)_2$ | $CH_3$ |
| A-29 | (R/S) $CH(CH_3)$—$CH(CH_3)_2$ | $CH_2CH_3$ |
| A-30 | (R) $CH(CH_3)$—$CH(CH_3)_2$ | H |
| A-31 | (R) $CH(CH_3)$—$CH(CH_3)_2$ | $CH_3$ |
| A-32 | (R) $CH(CH_3)$—$CH(CH_3)_2$ | $CH_2CH_3$ |
| A-33 | (S) $CH(CH_3)$—$CH(CH_3)_2$ | H |
| A-34 | (S) $CH(CH_3)$—$CH(CH_3)_2$ | $CH_3$ |
| A-35 | (S) $CH(CH_3)$—$CH(CH_3)_2$ | $CH_2CH_3$ |
| A-36 | (R/S) $CH(CH_3)$—$C(CH_3)_3$ | H |
| A-37 | (R/S) $CH(CH_3)$—$C(CH_3)_3$ | $CH_3$ |
| A-38 | (R/S) $CH(CH_3)$—$C(CH_3)$ | $CH_2CH_3$ |
| A-39 | (R) $CH(CH_3)$—$C(CH_3)_3$ | H |
| A-40 | (R) $CH(CH_3)$—$C(CH_3)_3$ | $CH_3$ |
| A-41 | (R) $CH(CH_3)$—$C(CH_3)_3$ | $CH_2CH_3$ |
| A-42 | (S) $CH(CH_3)$—$C(CH_3)_3$ | H |
| A-43 | (S) $CH(CH_3)$—$C(CH_3)_3$ | $CH_3$ |
| A-44 | (S) $CH(CH_3)$—$C(CH_3)_3$ | $CH_2CH_3$ |
| A-45 | (R/S) $CH(CH_3)$—$CF_3$ | H |
| A-46 | (R/S) $CH(CH_3)$—$CF_3$ | $CH_3$ |
| A-47 | (R/S) $CH(CH_3)$—$CF_3$ | $CH_2CH_3$ |
| A-48 | (R) $CH(CH_3)$—$CF_3$ | H |
| A-49 | (R) $CH(CH_3)$—$CF_3$ | $CH_3$ |
| A-50 | (R) $CH(CH_3)$—$CF_3$ | $CH_2CH_3$ |
| A-51 | (S) $CH(CH_3)$—$CF_3$ | H |
| A-52 | (S) $CH(CH_3)$—$CF_3$ | $CH_3$ |
| A-53 | (S) $CH(CH_3)$-$CF_3$ | $CH_2CH_3$ |
| A-54 | (R/S) $CH(CH_3)$—$CCl_3$ | H |
| A-55 | (R/S) $CH(CH_3)$—$CCl_3$ | $CH_3$ |
| A-56 | (R/S) $CH(CH_3)$—$CCl_3$ | $CH_2CH_3$ |
| A-57 | (R) $CH(CH_3)$—$CCl_3$ | H |
| A-58 | (R) $CH(CH_3)$—$CCl_3$ | $CH_3$ |
| A-59 | (R) $CH(CH_3)$—$CCl_3$ | $CH_2CH_3$ |
| A-60 | (S) $CH(CH_3)$—$CCl_3$ | H |
| A-61 | (S) $CH(CH_3)$—$CCl_3$ | $CH_3$ |
| A-62 | (S) $CH(CH_3)$—$CCl_3$ | $CH_2CH_3$ |
| A-63 | $CH_2CF_2CF_3$ | H |
| A-64 | $CH_2CF_2CF_3$ | $CH_3$ |
| A-65 | $CH_2CF_2CF_3$ | $CH_2CH_3$ |
| A-66 | $CH_2(CF_2)_2CF_3$ | H |
| A-67 | $CH_2(CF_2)_2CF_3$ | $CH_3$ |
| A-68 | $CH_2(CF_2)_2CF_3$ | $CH_2CH_3$ |
| A-69 | $CH_2C(CH_3){=}CH_2$ | H |
| A-70 | $CH_2C(CH_3){=}CH_2$ | $CH_3$ |
| A-71 | $CH_2C(CH_3){=}CH_2$ | $CH_2CH_3$ |
| A-72 | cyclopentyl | H |
| A-73 | cyclopentyl | $CH_3$ |
| A-74 | cyclopentyl | $CH_2CH_3$ |
| A-75 | cyclohexyl | H |
| A-76 | cyclohexyl | $CH_3$ |
| A-77 | cyclohexyl | $CH_2CH_3$ |
| A-78 | —$(CH_2)_4$— | |
| A-79 | —$CH(CH_3)(CH_2)_3$— | |
| A-80 | —$CH_2CH(CH_3)(CH_2)_2$— | |
| A-81 | —$(CH_2)_5$— | |
| A-82 | —$(CH_2)_2CH(CH_3)(CH_2)_2$— | |
| A-83 | —$CH_2CH(CH_3)CH_2CH(CH_3)CH_2$— | |
| A-84 | —$(CH_2)_2CH{=}CHCH_2$— | |
| A-85 | —$(CH_2)_2C(CH_3){=}CHCH_2$— | |
| A-86 | —$(CH_2)_2CHF(CH_2)_2$— | |
| A-87 | —$(CH_2)_3CHFCH_2$— | |
| A-88 | —$(CH_2)_2CH(CF_3)(CH_2)_2$— | |
| A-89 | —$(CH_2)_2O(CH_2)_2$— | |
| A-90 | —$(CH_2)_2S(CH_2)_2$— | |
| A-91 | —$CH_2CH{=}CHCH_2$— | |

The compounds I are suitable for use as fungicides. They have outstanding activity against a broad spectrum of phytopathogenic fungi, in particular from the class of the *Ascomycetes, Deuteromycetes, Phycomycetes* and *Basidiomycetes*. Some of them act systemically, and they can be employed in crop protection as foliar- and soil-acting fungicides.

They are especially important for controlling a large number of fungi on a variety of crop plants such as wheat, rye, barley, fats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Bipolaris* and *Drechslera* species on cereals, rice and turf,
*Blumeria graminis* (powdery mildew) on cereals,
*Botrytis cinerea* (gray mold) on strawberries, vegetables, ornamentals and grapevines,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawn,
*Septoria tritici* and *Stagonospora nodorum* on wheat,
*Uncinula necator* on grapevines,
*Ustilago* species on cereals and sugar cane, and also
*Venturia* species (scab) on apples and pears.

Moreover, the compounds I are suitable for controlling harmful fungi such as *Paecilomyces variotii* in the protection of materials (e.g. wood, paper, paint dispersions, fibers and fabrics) and in the protection of stored products.

The compounds I are applied by treating the fungi or the plants, seeds, materials or the soil to be protected against fungal infection with a fungicidally active amount of the active compounds. Application can be effected both before and after infection of the materials, plants or seeds by the fungi.

In general, the fungicidal compositions comprise from 0.1 to 95, preferably 0.5 to 90, % by weight of active compound.

When used in crop protection, the rates of application are from 0.01 to 2.0 kg of active compound per ha, depending on the nature of the desired effect.

In the treatment of seed, amounts of active compound of from 0.001 to 1 g, preferably 0.01 to 0.05 g, are generally required per kilogram of seed.

When used in the protection of materials or stored products, the rate of application of active compound depends on the nature of the field of application and on the desired effect. Rates of application conventionally used in the protection of materials are, for example, from 0.001 g to 2 kg, preferably 0.005 g to 1 kg, of active compound per cubic meter of material treated.

The compounds I can be converted into the customary formulations, e.g. solutions, emulsions, suspensions, dusts, powders, pastes and granules. The use form depends on the particular purpose; in any case, it should ensure a fine and uniform distribution of the compound according to the invention.

The formulations are prepared in a known manner, e.g. by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ether, furthermore condensates of sulfonated naphthalene and naphthalene derivatives with formaldehyde, condensates of naphthalene or of napthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristerylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydro-naphthalene, alkylated naphthalenes or their derivatives, methanol, ethanol, propanol, butanol, cyclohexanol, cyclohexanone, isophorone, strongly polar solvents, e.g. dimethyl sulfoxide, N-methylpyrrolidone or water.

Powders, materials for spreading and dusts can be prepared by mixing or concomitantly grinding the active substances with a solid carrier.

Granules, e.g. coated granules, impregnated granules and homogeneous granules, can be prepared by binding the active compounds to solid carriers. Examples of solid carriers are mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are in this case employed in a purity of from 90% to 100%, preferably 95% to 100% (according to NMR spectrum).

The Following Are Exemplary Formulations:

1. Products for Dilution with Water

A Soluble Concentrates (SL)

10 parts by weight of a compound according to the invention are dissolved in water or in a water-soluble solvent. As an alternative, wetters or other auxiliaries are added. The active compound dissolves upon dilution with water.

B Dispersible Concentrates (DC)

20 parts by weight of a compound according to the invention are dissolved in cyclohexanone with addition of a dispersant, for example polyvinylpyrrolidone. Dilution with water gives a dispersion.

C Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D Emulsions (EW, EO)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturrax) and made into a homogeneous emulsion. Dilution with water gives an emulsion.

E Suspensions (SC, OD)

In an agitated ball mill, 20 parts by weight of a compound according to the invention are comminuted with addition of dispersant, wetters and water or an organic solvent to give a fine active compound suspension. Dilution with water gives a stable suspension of the active compound.

F Water-Dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G Water-Dispersible Powders and Water-Soluble Powders (WP, SP)

75 parts by weight of a compound according to the invention are ground in a rotor-stator mill with addition of dispersant, wetters and silica gel. Dilution with water gives a stable dispersion or solution of the active compound.

2. Products to be Applied Undiluted

H Dustable Powders (DP)

5 parts by weight of a compound according to the invention are ground finely and mixed intimately with 95% of finely divided kaolin. This gives a dustable product.

I Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J ULV Solutions (UL)

10 parts by weight of a compound according to the invention are dissolved in an organic solvent, for example xylene. This gives a product to be applied undiluted.

The active compounds can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they are intended to ensure the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within substantial ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even the active compound without additives.

Various types of oils, wetting agents, adjuvants, herbicides, fungicides, other pesticides, or bactericides may be added to the active compounds, if appropriate also just prior to use (tank mix). These agents can be admixed with the agents according to the invention in a weight ratio of 1:10 to 10:1.

In the use form as fungicides, the compositions according to the invention can also be present together with other active compounds, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph anilinopyrimidines such as pyrimethanil, mepanipyrim or cyrodinyl, antibiotics such as cycloheximide, griseofulvin, kasugamycin, natamycin, polyoxin or streptomycin, azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, dicarboximides such as iprodion, myclozolin, procymidon, vinclozolin,

- dithiocarbamates such as ferbam, nabam, maneb, mancozeb, metam, metiram, propineb, polycarbamate, thiram, ziram, zineb,
- heterocylic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole, triforine,
- copper fungicides such as Bordeaux mixture, copper acetate, copper oxychloride, basic copper sulfate,
- nitrophenyl derivatives such as binapacryl, dinocap, dinobuton, nitrophthalisopropyl
- phenylpyrroles such as fenpiclonil or fludioxonil,
- sulfur
- other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamide
- strobilurins such as azoxystrobin, dimoxystrobin, fluoxastrobin, kresoxim-methyl, metominostrobin, orysastrobin, picoxystrobin, pyraclostrobin or trifloxystrobin,
- sulfenic acid derivatives such as captafol, captan, dichlofluanid, folpet, tolylfluanid
- cinnamides and analogs such as dimethomorph, flumetover or flumorph.

SYNTHESIS EXAMPLES

With due modification of the starting compounds, the procedures shown in the synthesis examples below were used to obtain further compounds I. The resulting compounds, together with physical data, are listed in the table below.

Example 1

Preparation of ethyl 2-cyclopentyl-3-oxobutanoate

A mixture of ethyl 3-oxobutanoate (0.5 mol), cyclopentyl bromide (0.5 mol) and sodium ethoxide (0.5 mol) in ethanol (100 ml) was heated under reflux for 15 hours. The reaction mixture was cooled to about 20-25° C., and 71 g of the title compound were then isolated by distillation (96-100° C., 0.25 mbar).

Example 2

Preparation of 5-methyl-6-cyclopentyl-7-hydroxy-[1,2,4]triazolo[1,5-a]pyrimidine A mixture of 3-amino-1,2,4-triazole (14 g), ethyl 2-cyclopentyl-3-oxobutanoate (0.17 mol, Ex. 1) and tributylamine (50 ml) was heated at 180° C. for 6 hours. The reaction mixture was cooled to about 70° C., and aqueous NaOH solution (21 g in 200 ml of $H_2O$) was then added and the solution was stirred for another 30 min. Following phase separation and extraction with diethyl ether, the aqueous phase was acidified with conc. HCl solution. The precipitate gave 19 g of the title compound.

Example 3

Preparation of 5-methyl-6-cyclopentyl-7-chloro[1,2,4]triazolo-[1,5-a]pyrimidine A mixture of 5-methyl-6-cyclopentyl-7-hydroxy[1,2,4]triazolo[1,5-a]pyrimidine (17 g, Ex. 2) and $POCl_3$ (50 ml) was heated under reflux for 8 hours. During this operation, some of the $POCl_3$ was distilled off. The residue was poured into a mixture of dichloromethane and water. The organic phase was separated off and dried. Removal of the solvent gave 11 g of the title compound of m.p. 87° C.

Example 4

Preparation of 5-methyl-6-cyclopentyl-7-(4-methylpiperidin-1-yl)-[1,2,4]triazolo[1,5-a]pyrimidine [I-1]

With stirring, a solution of 4-methylpiperidine (1.5 mmol) and triethylamine (1.5 mmol) in 10 ml of dichloromethane was added to a solution of 5-methyl-6-cyclopentyl-7-chloro[1,2,4]triazolo[1,5-a]pyrimidine (1.5 mmol, Ex. 3) in 20 ml of dichloromethane. The reaction mixture was stirred at 20-25° C. for about 16 hours and then washed with a 5% strength solution of HCl. The organic phase was separated off and dried. Following distillative removal of the solvent and chromatography on silica gel, this gave 0.26 g of the title compound of m.p. 145° C.

TABLE I

Compounds of the formula I

| No. | $R^1$ | $R^2$ | $R^3$ | X | phys. data (m.p. [° C.]; IR [$cm^{-1}$]) |
|---|---|---|---|---|---|
| I-1 | $—(CH_2)_2CH(CH_3)(CH_2)_2—$ | | cyclopentyl | $CH_3$ | 145 |
| I-2 | (R) $CH(CH_3)—CH(CH_3)_2$ | H | cyclopentyl | $CH_3$ | 96 |
| I-3 | (S) $CH(CH_3)—CF_3$ | H | cyclopentyl | $CH_3$ | 108 |
| I-4 | H | H | cyclopentyl | $CH_3$ | 271 |
| I-5 | $CH_3$ | H | cyclopentyl | $CH_3$ | 175 |
| I-6 | (R) $CH(CH_3)—C(CH_3)_3$ | H | cyclopentyl | $CH_3$ | 1960; 1605; 1590; 1240 |

EXAMPLES OF THE ACTION AGAINST HARMFUL FUNGI

The fungicidal action of the compounds of the formula I was demonstrated by the following experiments:

The active compounds were formulated separately as a stock solution comprising 0.25% by weight of active compound in acetone or DMSO. 1% by weight of the emulsifier Uniperol® EL (wetting agent having emulsifying and dispersing action based on ethoxylated alkylphenols) was added to this solution. The stock solutions of the active compounds were diluted with water to the stated concentration.

Example 1

Activity Against Early Blight of Tomato Caused by *Alternaria solani*

Leafs of potted plants of the cultivar "Groβe Fleischtomate St. Pierre" were sprayed to run off point with an aqueous suspension having the concentration of active compound stated below. The next day, the leaves were infected with an aqueous spore suspension of *Alternaria solani* in a 2% strength biomalt solution of a density of $0.17\times10^6$ spores/ml. The plants were then placed in a water-vapor-saturated chamber at 20-22° C. After 5 days, the early blight on the untreated but infected control plants had developed to such an extent that the infection could be determined visually in %.

In this test, the plants which had been treated with 250 ppm of active compound I-1 showed no infection, whereas the untreated plants were 90% infected.

Example 2

Activity Against Gray Mold on Bell Pepper Leaves Caused by *Botrytis cinerea*, Protective Application bell pepper seedlings of the cultivar "Neusiedler Ideal Elite" were, after 4-5 leaves were well developed, sprayed to run off point with an aqueous suspension of the concentration of active compound stated below. The next day, the treated plants were inoculated with a spore suspension of *Botrytis cinerea* which contained $1.7\times10^6$ spores/ml in a 2% strength aqueous biomalt solution. The test plants were then placed in a climatized chamber at 22-24° C. and high atmospheric humidity. After 5 days, the extent of the fungal infection on the leaves could be determined visually in %.

In this test, the plants which had been treated with 250 ppm of active compound I-1 or I-3 showed at most 20% of infection, whereas the untreated plants were 90% infected.

Example 3

Activity Against Mildew on Cucumber Leaves Caused by *Sphaerotheca fuliginea*, Protective Application Leaves of potted cucumber seedlings of the cultivar "Chinese Snake" were, at the cotyledone stage, sprayed to run off point with an aqueous suspension of the concentration of active compound stated below. 20 hours after the spray coating had dried on, the plants were inoculated with an aqueous spore suspension of mildew of cucumber (*Sphaerotheca fuliginea*). The plants were then cultivated in a greenhouse at 20-24° C. and 60-80% relative atmospheric humidity for 7 days. The extent of the mildew development was then determined visually in % infection of the cotyledone area.

In this test, the plants which had been treated with 250 ppm of active compound I-1 or I-3 showed an infection of not more than 3%, whereas the untreated plants were 90% infected.

We claim:

1. A compound of the formula I,

I where:

$R^1$, $R^2$ are hydrogen, $C_1$-$C_{10}$-alkyl, $C_2$-$C_{10}$-alkenyl, $C_2$-$C_{10}$-alkynyl, $C_1$-$C_{10}$-haloalkyl, $C_3$ $C_8$-cycloalkyl, phenyl, naphthyl; or 5- or 6-membered saturated, unsaturated or aromatic heterocyclyl which contains one to four nitrogen atoms or one to three nitrogen atoms and one sulfur or oxygen atom; or $R^1$ and $R^2$ together with the bridging nitrogen atom can form a 5- or 6-membered ring which contains one to four nitrogen atoms or one to three nitrogen atoms and one sulfur or oxygen atom;

if $R^1$ and $R^2$ are not hydrogen they can, independently of one another, be partially or fully halogenated and/or may carry one to three radicals from the group $R^a$ $R^a$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and unhalogenated or halogenated oxy-$C_1$-$C_4$-alkyleneoxy;

where these aliphatic, or alicyclic, groups for their part may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl, heterocyclyloxy, where the cyclic systems contain 3 to 10 ring members; aryl, aryloxy, arylthio, aryl-$C_1$-$C_6$-alkoxy, aryl-$C_1$-$C_6$-alkyl, hetaryl, hetaryloxy, hetarylthio, where the aryl radicals preferably contain 6 to 10 ring members, the hetaryl radicals contain 5 or 6 ring members, where the cyclic systems may be partially or fully halogenated or may be substituted by alkyl or haloalkyl groups;

$R_3$ is $C_3$-$C_{14}$-cycloalkyl or $C_6$-$C_{14}$-bicycloalkyl, where $R^3$ may be unsubstituted or partially or fully halogenated and/or may carry one to three radicals from the group $R^a$; and X is $C_1$-$C_6$-alkyl;

or a salt thereof.

2. A compound of the formula I as claimed in claim 1 where:

$R^1$, $R^2$ are hydrogen, $C_1$-$C_{10}$-alkyl, $C_2$-$C_{10}$-alkenyl, $C_2$-$C_{10}$- alkynyl, $C_1$-$C_{10}$-haloalkyl, $C_3$-$C_8$-cycloalkyl, phenyl, naphthyl; or 5- or 6-membered saturated, unsaturated or aromatic heterocyclyl which contains one to four nitrogen atoms or one to three nitrogen atoms and one sulfur or oxygen atom; or $R_1$and $R_2$ together with the bridging nitrogen atom can form a 5- or 6-membered ring which contains one to four nitrogen atoms or one to three nitrogen atoms and one sulfur or oxygen atom;

if $R_1$ and $R_2$ are not hydrogen they can, independently of one another, be partially or fully halogenated and/or may carry one to three radicals from the group $R^a$ $R^a$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$- $C_6$-haloalkoxy, $C_1$-$C_6$-alkylthio, $C_1$-$C_6$-alkylamino, di-$C_1$-$C_6$-alkylamino, $C_2$-$C_6$-alkenyl, $C_2$-$C_6$- alkenyloxy, $C_2$-$C_6$-alkynyl, $C_3$-$C_6$-alkynyloxy and unhalogenated or halogenated oxy-$C_1$-$C_4$- alkyleneoxy;

$R_3$ is $C_3$-$C_{14}$cycloalkyl or $C_6$-$C_{14}$-bicycloalkyl, where $R^3$ may be unsubstituted or partially or fully halogenated and/or may carry one to three radicals from the group $R^a$; and X is $C_1$-$C_6$-alkyl;

or a salt thereof.

3. A compound of the formula I as claimed in claim 1 or 2 in which X is methyl.

4. A process for preparing compounds of the formula I as claimed in claim 1, which comprises cyclizing dicarbonyl compounds of the formula II

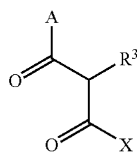

where A is $C_1$-$C_{10}$-alkoxy and $R^3$ and X are as defined for formula I with 3-amino-1,2,4-triazole to give 7-hydroxytriazolopyrimidines of the formula III

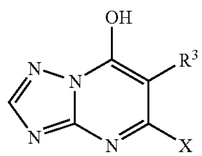

and halogenating III with a halogenating agent to give 7-halogentriazolopyrimidines of the formula IV

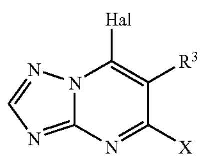

where Hal is halogen, followed by reaction with an amine of the formula V

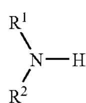

where $R^1$ and $R^2$ are as defined in formula I, to give 5-alkyl-7-aminotriazolopyrimidines of the formula I.

5. A compound of formula IV

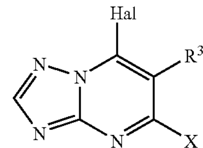

wherein Hal is halogen; $R^3$ is $C_3$-$C_{14}$-cycloalkyl or $C_6$-$C_{14}$-bicycloalkyl, where $R^3$ may be unsubstituted or partially or fully halogenated and/or may carry one to three radicals from the group $R^a$; $R^a$ is cyano, nitro, hydroxyl, $C_1$-$C_6$-alkyl, $C_1$-$C_6$- haloalkyl, $C_3$-$C_6$-cycloalkyl, $C_1$-$C_6$- alkoxy, $C_1$-$C_6$-haloalkoxy, $C_1$-$C_6$-alkylthio, $C_1$-$C_6$-alkylamino, di-$C_1$-$C_6$-alkylamino, $C_2$-$C_6$- alkenyl, $C_2$-$C_6$- alkenyloxy, $C_2$-$C_6$-alkynyl, $C_3$-$C_6$-alkynyloxy and unhalogenated or halogenated oxy-$C_1$-$C_4$-alkyleneoxy;where these aliphatic, or alicyclic, groups for their part may be partially or fully halogenated or may carry one to three groups $R^b$: $R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkyhhio, alkylaniino, dialkylamino, formyl, alkylcarbonyl, alkyl-sulfonyl, alkylsulfoxyl, alkoxycarbonyl, alkylcarbonyloxy, alkylaminocarbonyl, dialkyl-aminocarbonyl, alkylantinothiocarbonyl, dialkyl-minothiocarbonyl, where the alkyl groups in these radicals contain 1 to 6 carbon atoms and the alkenyl or alkynyl groups mentioned in these radicals contain 2 to 8 carbon atoms; and/or one to three of the following radicals:

cycloalkyl, cycloalkoxy, heterocyclyl, heterocyclyloxy, where the cyclic systems contain 3 to 10 ring members; aryl, aryloxy, arylthio, aryl-$C_1$-$C_6$-alkoxy, aryl-$C_1$-$C_6$alkyl, hetaryl, hetaryloxy, hetarylthio, where the aryl radicals preferably contain 6 to 10 ring members, the hetaryl radicals contain 5 or 6 ring members, where the cyclic systems may be partially or fully halogenated or may be substituted by alkyl or haloalkyl groups;

X is $C_1$-$C_6$-alkyl.

6. A method for treating seeds to control phytopathogenic harmful fungi which comprises treating seeds with the compounds of the formula I as claimed in claim 1 in an amount of from 0.001 to 1 g/kg.

7. A method for controlling phytopathogenic harmful fungi, which comprises treating the fungi or the materials, plants, the soil or the seeds to be protected against fungal attack with an effective amount of a compound of the formula I as claimed in claim 1.

8. A composition for controlling harmful fungi which comprises a fungicidal effective amount of at least one compound of formula I as claimed in claim 1 or a salt thereof, and at least one solvent and/or solid carrier.

9. The composition of claim 8, which comprises in addition an emulsifier or dispersant.

* * * * *